(12) United States Patent
Axelsson et al.

(10) Patent No.: US 7,544,181 B2
(45) Date of Patent: Jun. 9, 2009

(54) DISPOSABLE INJECTION SYRINGE

(75) Inventors: Robert Axelsson, Gränna (SE); Johan Rinman, Gränna (SE); Tomas Arnerdal, Bankeryd (SE)

(73) Assignee: Medsafe ASA, Oslo (NO)

( * ) Notice: Subject to any disclaimer, the term of this patent is extended or adjusted under 35 U.S.C. 154(b) by 0 days.

(21) Appl. No.: 11/293,033

(22) Filed: Dec. 2, 2005

(65) Prior Publication Data

US 2006/0178626 A1 Aug. 10, 2006

Related U.S. Application Data

(63) Continuation of application No. PCT/EP2004/005997, filed on Jun. 3, 2004.

(30) Foreign Application Priority Data

Jun. 4, 2003 (SE) .................................. 0301667

(51) Int. Cl.
*A61M 5/00* (2006.01)
*A61M 5/32* (2006.01)

(52) U.S. Cl. ...................... 604/110; 604/187; 604/195; 604/905

(58) Field of Classification Search ................ 604/905, 604/110, 192, 195, 197, 198, 218, 220, 227–229, 604/240, 243, 181, 187
See application file for complete search history.

(56) References Cited

U.S. PATENT DOCUMENTS

| | | | |
|---|---|---|---|
| 5,047,016 A * | 9/1991 | Dolgin et al. | 604/110 |
| 5,531,705 A * | 7/1996 | Alter et al. | 604/195 |
| 5,810,782 A | 9/1998 | Saito | 604/243 |
| 5,968,020 A | 10/1999 | Saito | 604/243 |
| 6,926,698 B2 * | 8/2005 | Lin | 604/198 |
| 7,179,243 B2 * | 2/2007 | Chen | 604/110 |
| 2001/0021821 A1 * | 9/2001 | Wang et al. | 604/110 |

FOREIGN PATENT DOCUMENTS

| FR | 2 658 724 | 8/1991 |
|---|---|---|
| WO | WO 91/03268 | 3/1991 |

* cited by examiner

*Primary Examiner*—Kevin C Sirmons
*Assistant Examiner*—Bhisma Mehta
(74) *Attorney, Agent, or Firm*—Winston & Strawn LLP

(57) ABSTRACT

A disposable injection syringe for allowing a comfortable injection at a low injury risk of the user. The syringe includes an injection needle, a tubular cylinder having a free opening at a first end, an end part with a through hole for slidably accommodating the injection needle at an opening of a second end of the tubular cylinder opposite the free opening, a piston reciprocally accommodated in the cylinder, a piston rod attached to the piston and extending into the cylinder through the free opening of the cylinder, a coupling for interlocking the piston and the injection needle at least in the reverse direction of the injection piston stroke. The coupling has two coupling parts, one of which is attached to the piston and the other of which is attached to the injection needle. The coupling parts are spaced from each other during at least part of the injection stroke and interlock during withdrawal.

12 Claims, 10 Drawing Sheets

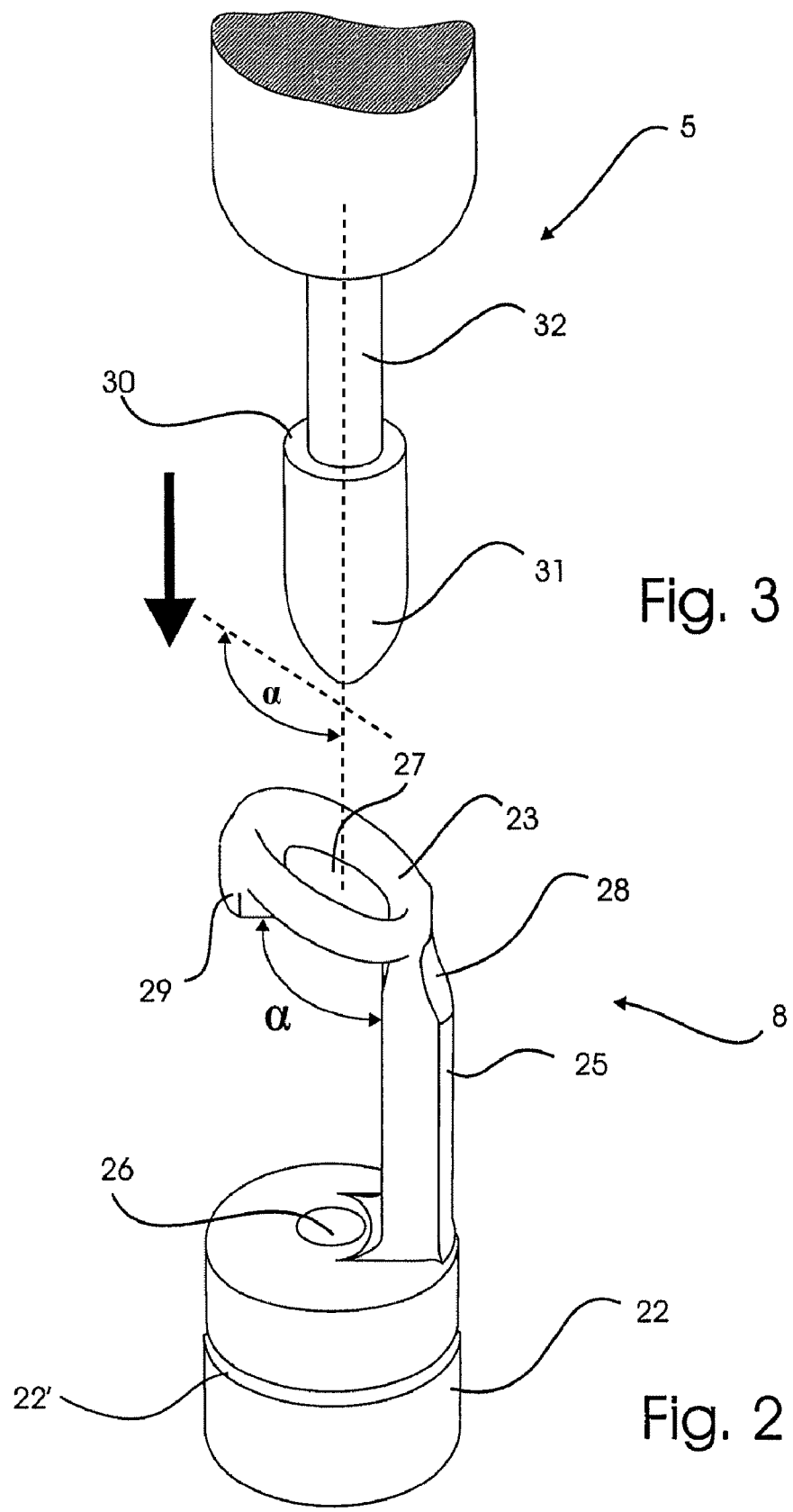

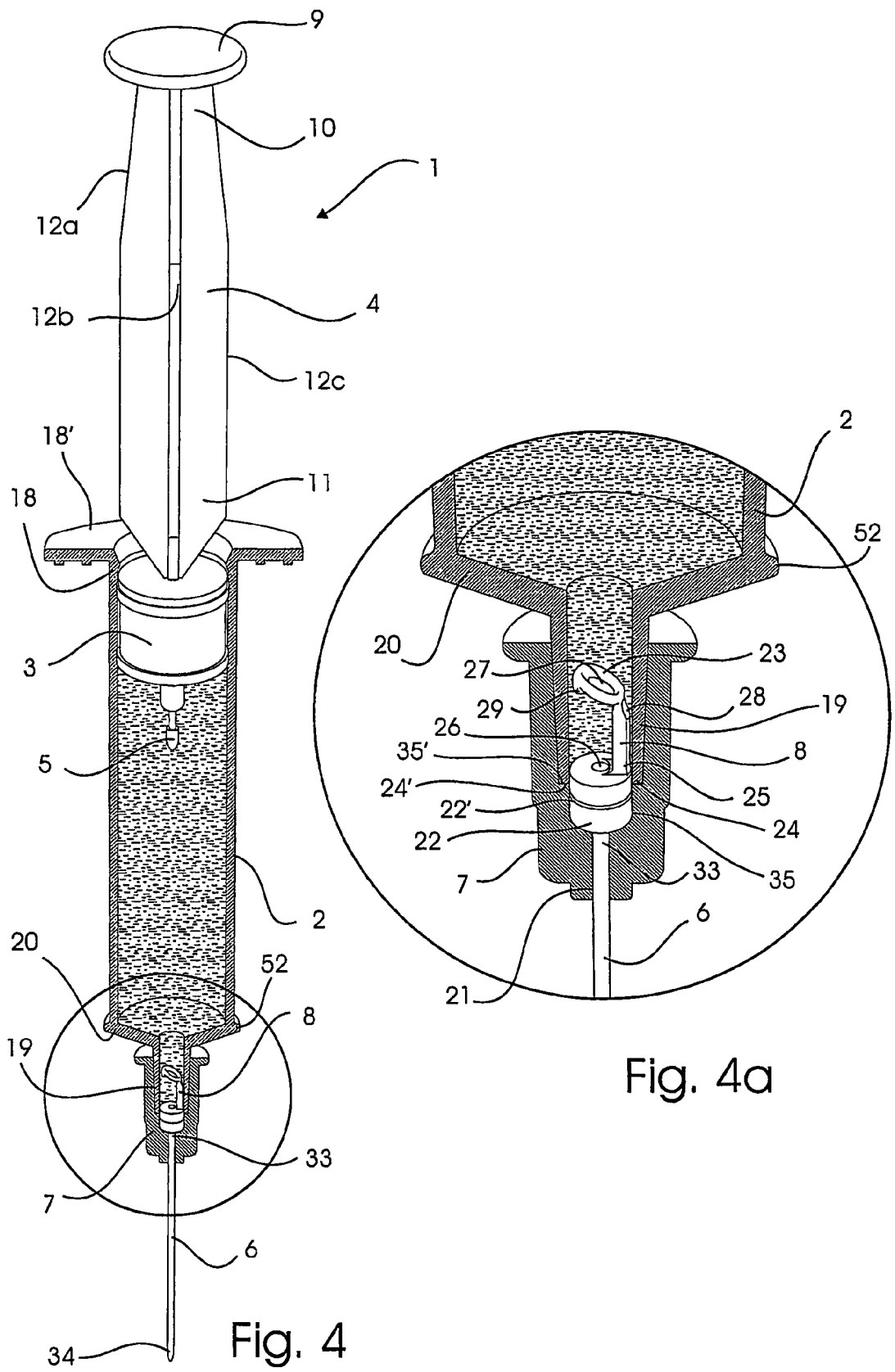

Figure 1:
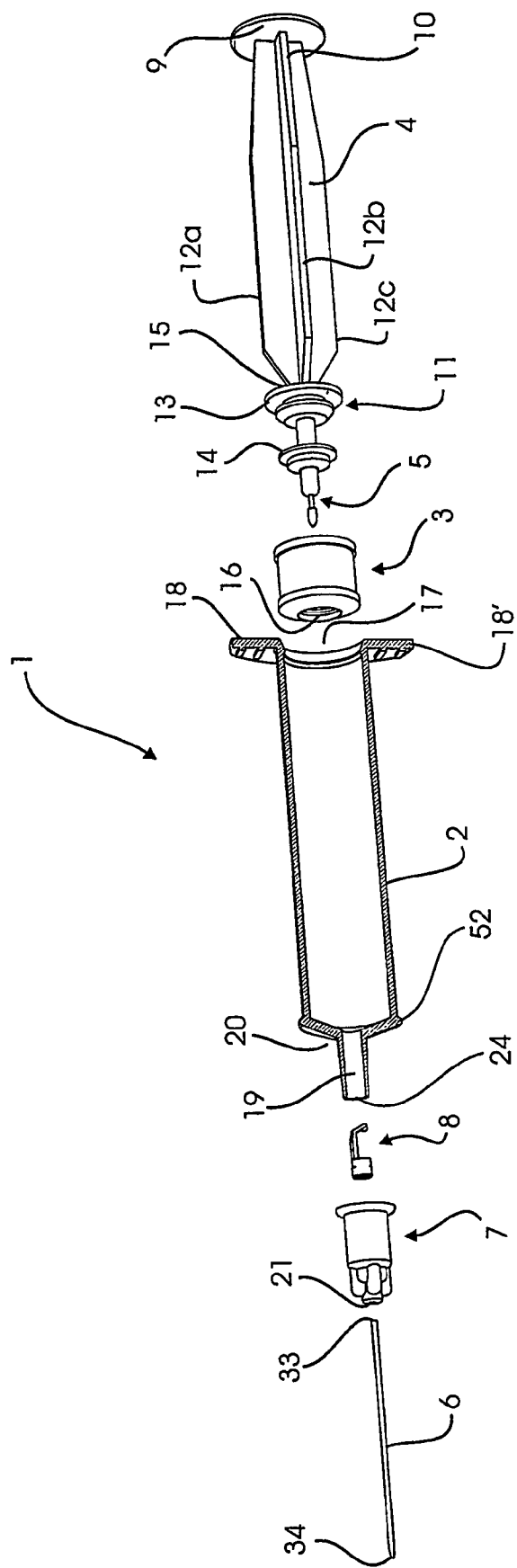

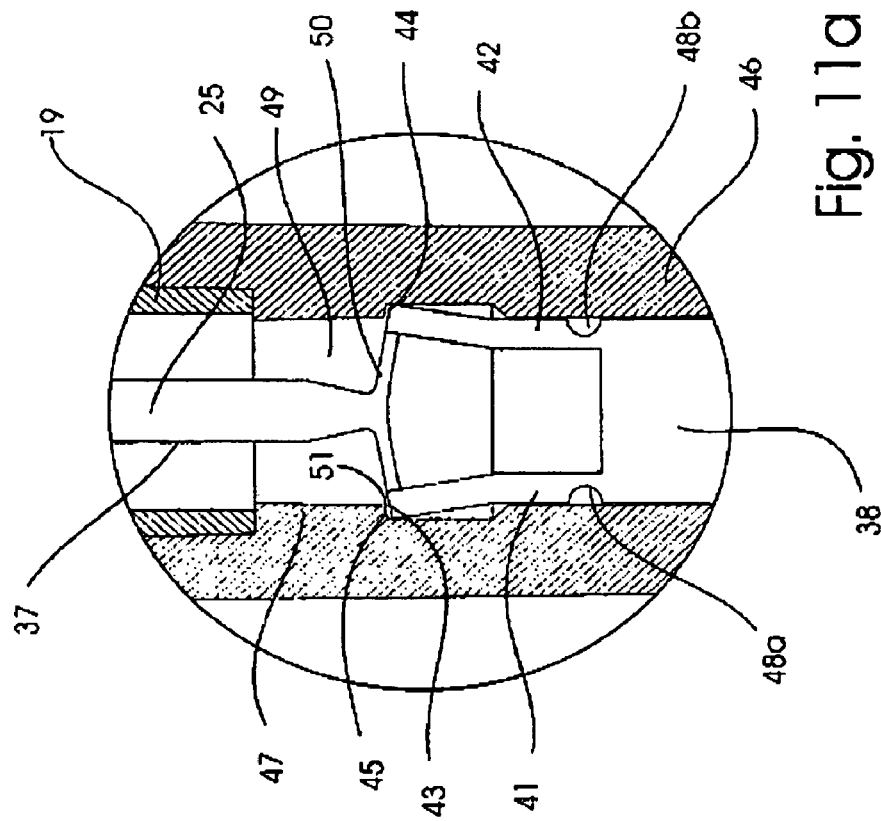
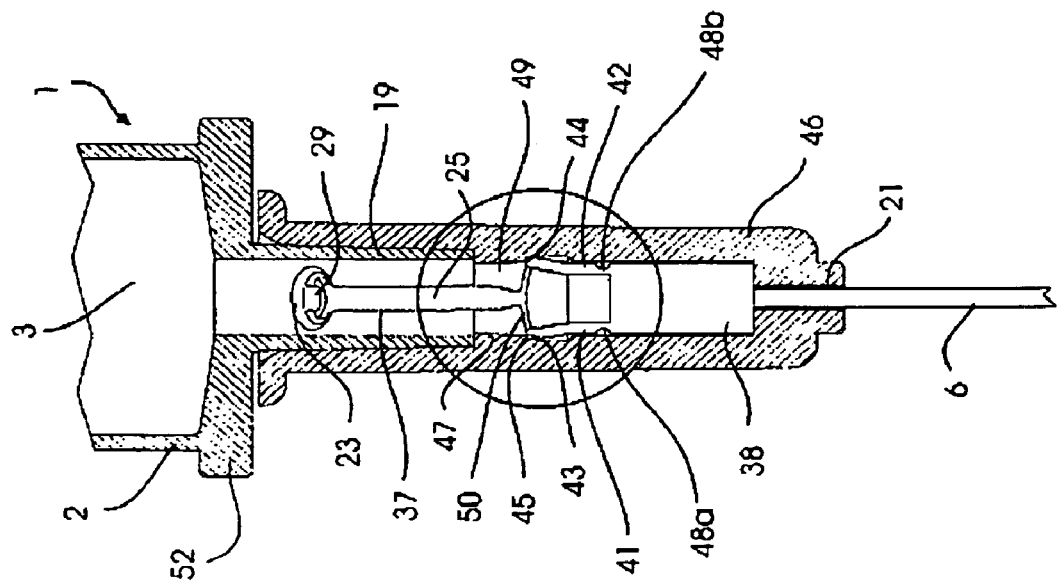

DISPOSABLE INJECTION SYRINGE

CROSS-REFERENCE TO RELATED APPLICATIONS

This application is a continuation of International application PCT/EP2004/005997 filed Jun. 3, 2004, the entire content of which is expressly incorporated herein by reference thereto.

BACKGROUND

The present invention relates to a disposable injection syringe comprising an injection needle, a tubular cylinder with a free opening at a first end, an end part with a through hole for slidably accommodating the injection needle at an opening of a second end of the tubular cylinder opposite the free opening, a piston reciprocally accommodated in the cylinder, a piston rod attached to the piston and extending into the cylinder through the free opening of the cylinder, a coupling for interlocking the piston and the injection needle at least in the reverse direction of the injection piston stroke, wherein the coupling further comprises two coupling parts, a male coupling part which is attached to the piston and a female coupling part which is attached to the injection needle or vice versa, said coupling parts being spaced from each other during at least part of the injection stroke.

Known disposable syringes should be discarded to reduce the risk of getting or spreading an infection but it is often possible to reuse them. Such disposable syringes are often expensive to manufacture and therefore expensive to use, and in spite of safety regulations and injection control guidelines many persons and health authorities especially in poor countries violate these guidelines. In addition, many drug abusers unhesitatingly utilize the same contaminated syringe and needle without prior sterilisation, or several drug abusers share the same syringe and needle, thereby contributing to the spreading of blood borne, infectious diseases such as HIV virus (AIDS) and hepatitis B.

In order to prevent such reuses of disposable syringes, different disposable syringes have been developed, some of them being needleless systems as a safeguard against contamination and as a precaution against needle sticks for healthcare providers. However, even with needleless systems the reuse of syringes from patient to patient is widespread. Moreover, for the administration of many different medicaments, needleless systems cannot be used.

European Patent EP 0 639 992 B1 discloses a disposable prefilled syringe. This syringe has a cannula frictionally mounted inside the outlet connection piece or needle carrier. The inner edge of opposing piston rod legs are provided with barbs arranged to cooperate with ratchet means provided on the piston rod in order to interlock these two parts of the syringe thereby disenabling refilling of the syringe and preventing a further injection possibility. Following injection the piston is retracted bringing the needle along for accommodation into the interior of the cylinder.

Significant compressive forces are needed for performing the injection to secure the frictional engagement of ratchet and barbs. Also, some patients will be able to feel the stepwise engagement between the ratchets and the barbs during injection. The jerky motion of the piston when the barbs and ratchet snap together during the injection procedure is felt as an uneven and inconvenient experience by the patient. Furthermore, the many structural members of the syringe that need to co-operate nicely for producing a reliable interlocking contribute to increased manufacturing costs.

Another disposable injection syringe is known from British patent application 2,256,146-A. This syringe has a piston rod, which is connected to the piston by a single use connection. The connection breaks when the syringe has been completely discharged or if an attempt is made to reuse the syringe. The piston is designed with a hollow space for receiving and containing the needle when this has been detached from the syringe end after use.

This kind of syringe presents a high risk of pricking oneself when the piston rod is to be mounted over the needle tip for enclosing and hiding the needle.

European patent application EP 0 824 924 A1 discloses a disposable syringe provided with a needle holder for internal mounting of the needle hub of the needle. An arrowhead-like retainer rod on the piston is forced into a close fitting engagement with a complementarily shaped arrowhead-like retaining hole, to interlock with said hole in the direction of the injection stroke. Since the needle is situated inside the holder, both holder and needle is, after finishing of the injection procedure, for safety reasons retracted into the syringe chamber.

However, this known disposable syringe has several disadvantages. For one thing the needle holder is capable of being pressed inside the housing during preliminary mounting of the needle, thereby creating leakage between the holder and the outlet orifice of the syringe and rendering the syringe useless. Moreover the interlocking of rod and hole is not smooth and will unavoidable be felt by the patient.

U.S. Pat. No. 6,066,115 describes another disposable syringe of substantially similar design to the one described in EP 0 824 924. Both these known syringes require a relative large compression force in order to obtain coupling between the engagement parts.

Thus, there is a need for a syringe that overcomes the drawbacks of prior art syringes.

This need is now satisfied by the present invention.

SUMMARY OF THE INVENTION

The present invention relates to a disposable syringe of the kind mentioned in the opening paragraph, that has a simple structure, is easy to operate, is inexpensive to manufacture, and cannot be reused. This syringe also provides a lower risk of the user being injured by the needle than previously known syringes, while also allowing for a comfortable injection. Furthermore, in the present syringe system, the risk of accidentally rendering the syringe useless, when the needle is mounted on the syringe, is eliminated.

To provide these advantages, the present invention relates to a disposable syringe comprising an injection needle, a tubular cylinder having first and second ends with a free opening at the first end, an end part having a through hole for slidably accommodating the injection needle at the second end of the cylinder, a piston reciprocally accommodated in the cylinder for movement toward and away from the needle, a piston rod attached to the piston and extending into the cylinder through the free opening at the first end of the cylinder, and a coupling for interlocking the piston and the injection needle at least when the piston moves away from the needle. The coupling further comprises male and female coupling parts, one of which is attached to the piston and the other of which is attached to the injection needle, with the coupling parts being initially spaced from each other. The female coupling part comprises a coupling ring and the male coupling part comprises a coupling barb for interlocking with the coupling ring.

Preferably, the piston is attached to the male coupling part and the injection needle is attached to the female coupling part. Also, the needle hub is configured for mounting on the second end of the cylinder and for closing an orifice of the second end of the cylinder.

BRIEF DESCRIPTION OF THE DRAWING FIGURES

Figure 5:
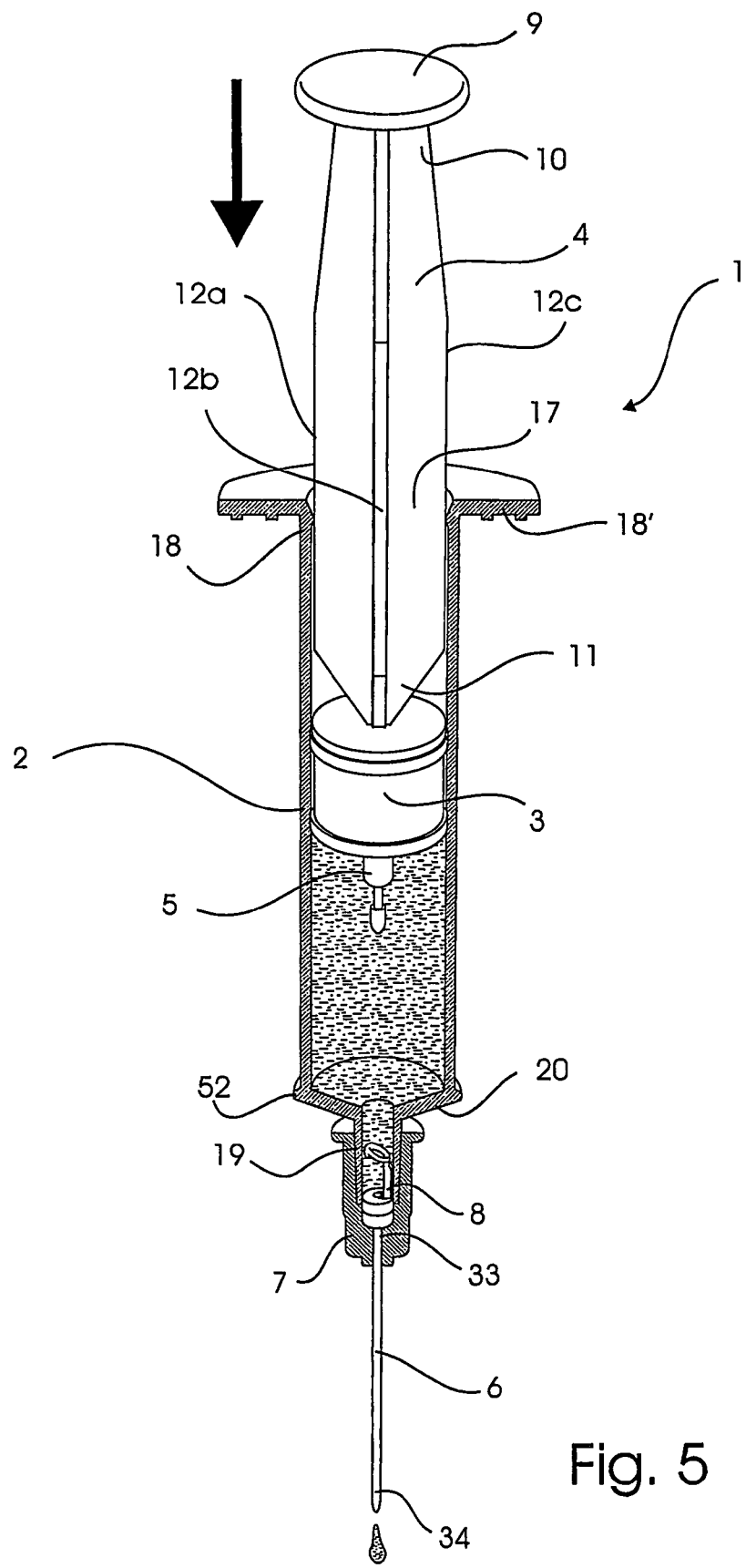
Figures 6, 6A:
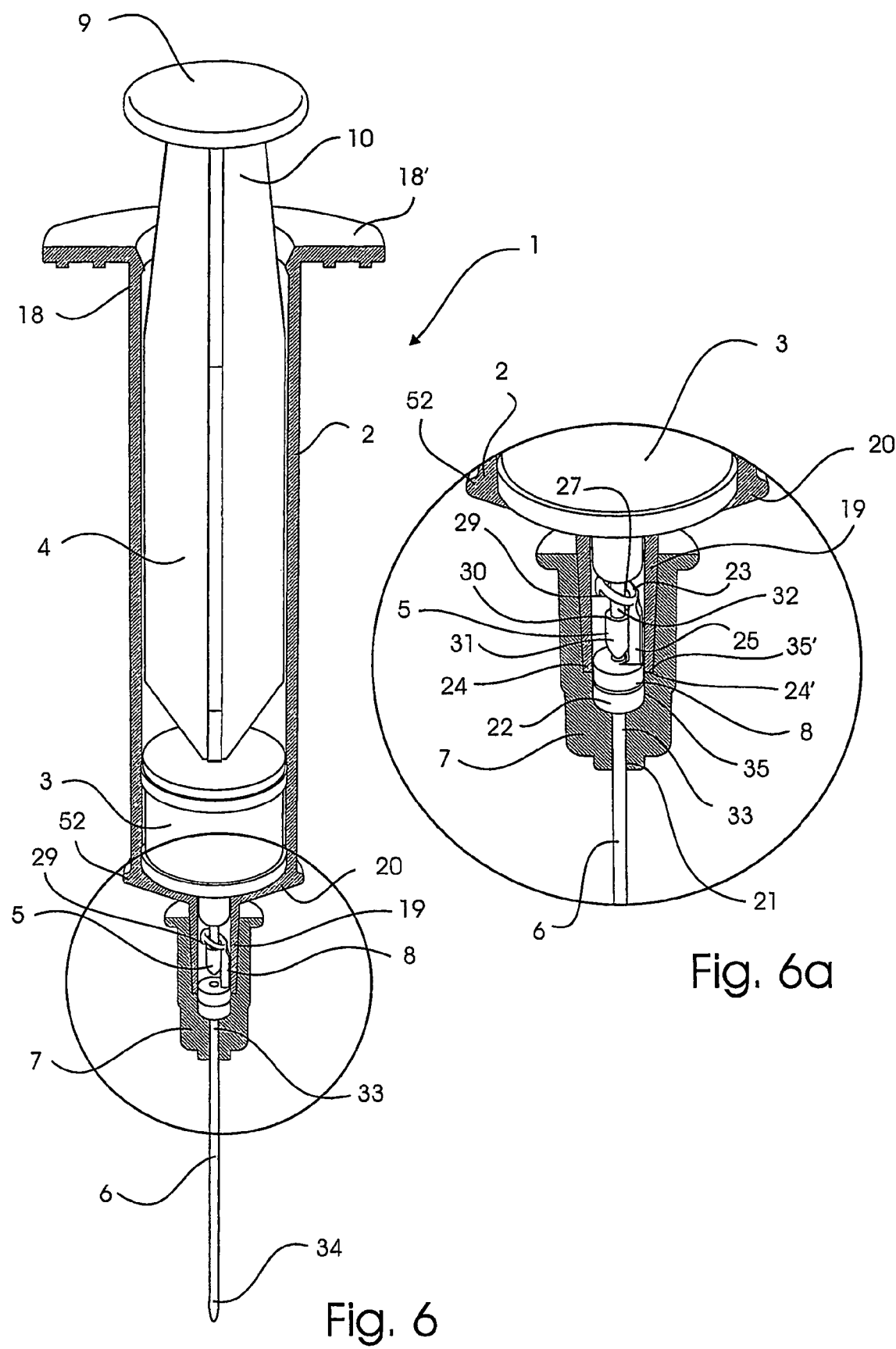
Figures 7, 7A:
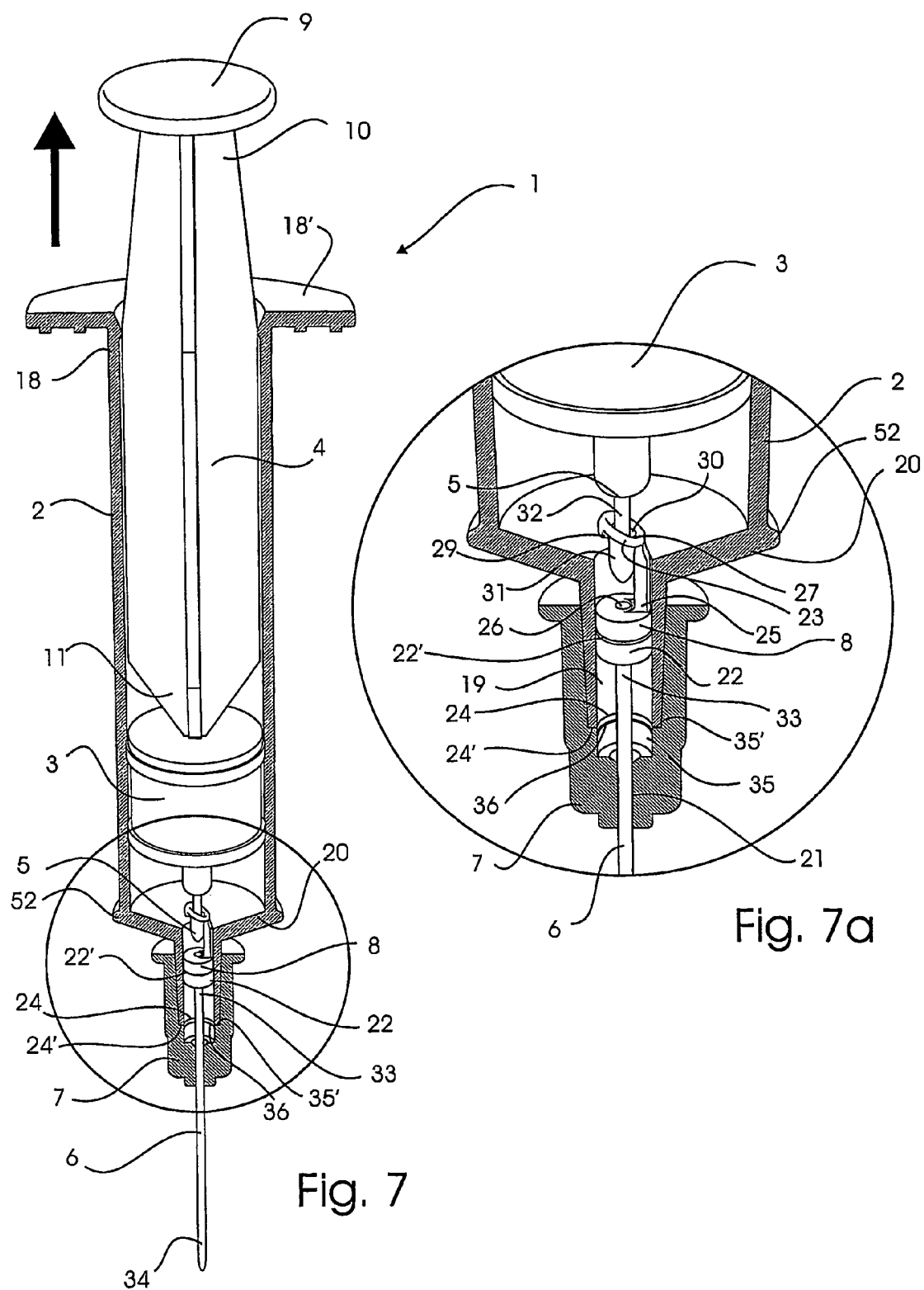
Figure 8:
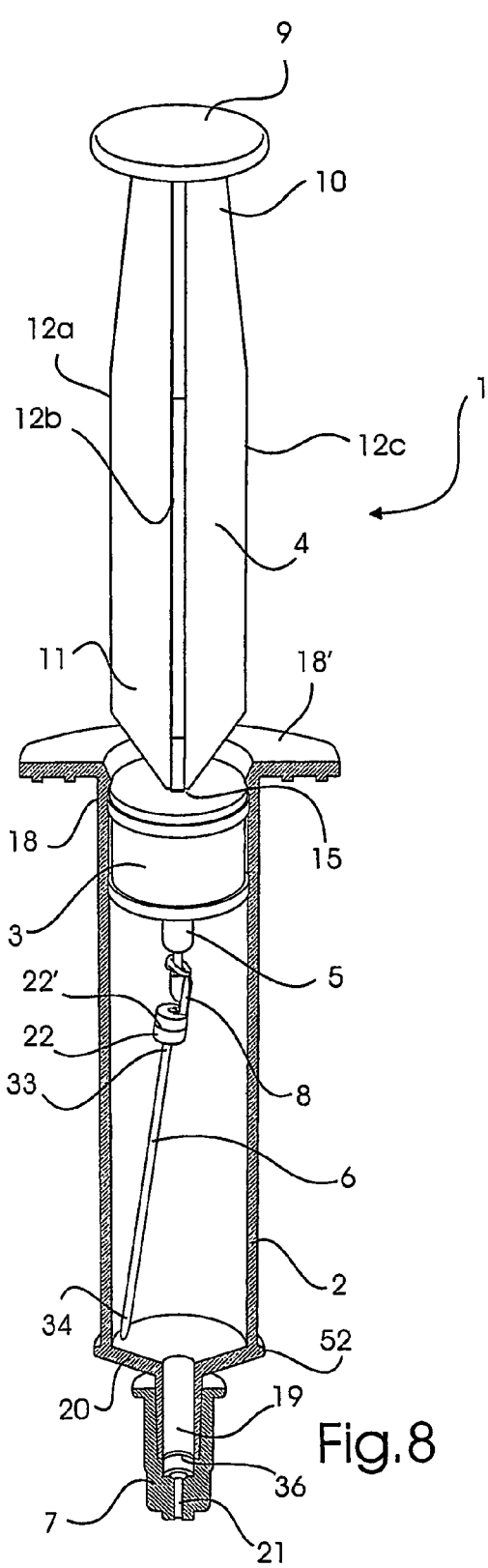
Figure 9:
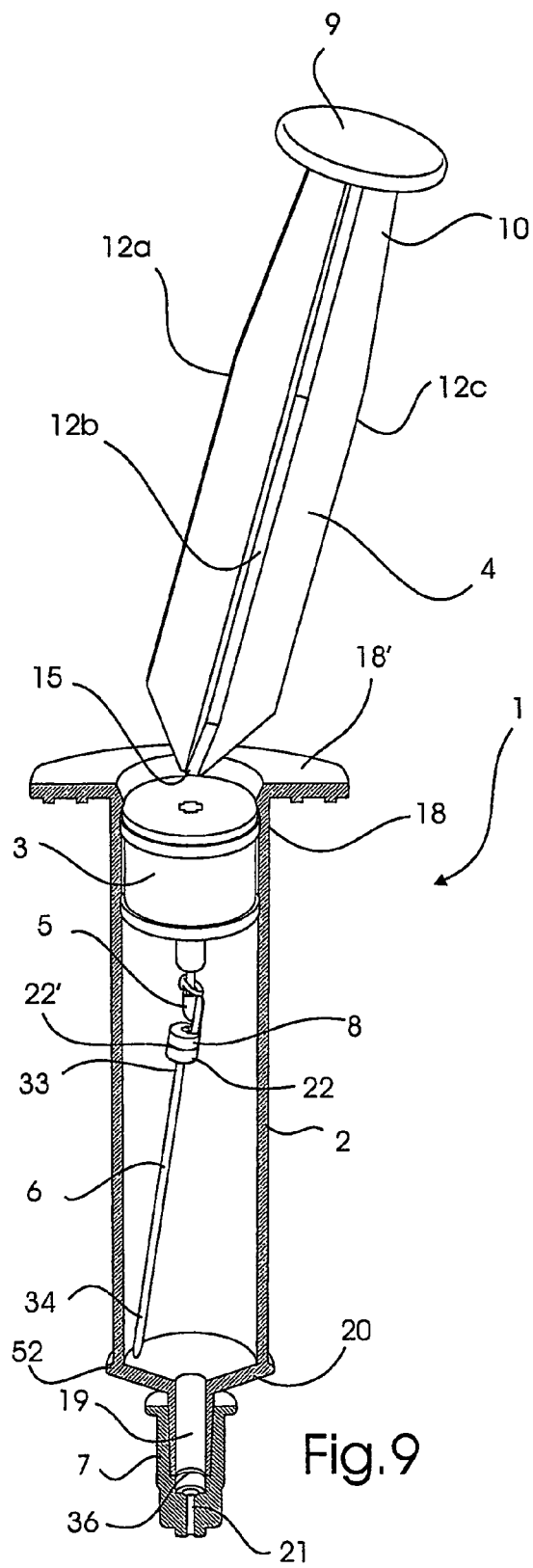

The invention will be explained in greater detail below, giving further advantageous features and technical effects and describing an exemplary embodiment with reference to the drawing, in which FIG. 1 is an exploded view partly in longitudinal cross-section of a disposable injection syringe according to the invention, FIG. 2 is a perspective view of a female coupling part according to the invention, FIG. 3 is a perspective view of a male coupling part according to the invention, FIG. 4 is the syringe seen in FIG. 1 in an assembled condition filled and prepared for injection and with the syringe cylinder and needle hub shown intersected for the purpose of illustration, FIG. 4a is an enlarged view of the outlet end of the syringe shown in FIG. 4, FIG. 5 is the syringe seen in FIG. 4 halfway through the injection stroke, FIG. 6 is the syringe seen in FIG. 4 at the end of the injection stroke where the syringe is emptied, FIG. 6a is an enlarged view of the outlet end of the syringe shown in FIG. 6, FIG. 7 is the syringe seen in FIG. 4 at the beginning of the withdrawal of the piston, FIG. 7a is an enlarged view of the outlet end of the syringe shown in FIG. 7 during withdrawal of the piston and the injection needle, FIG. 8 is the syringe seen in FIG. 4 with the injection needle fully retracted and angled, accommodated inside the syringe cylinder, and FIG. 9 is the syringe seen in the position of FIG. 8 with the piston rod broken off.

Figure 10:
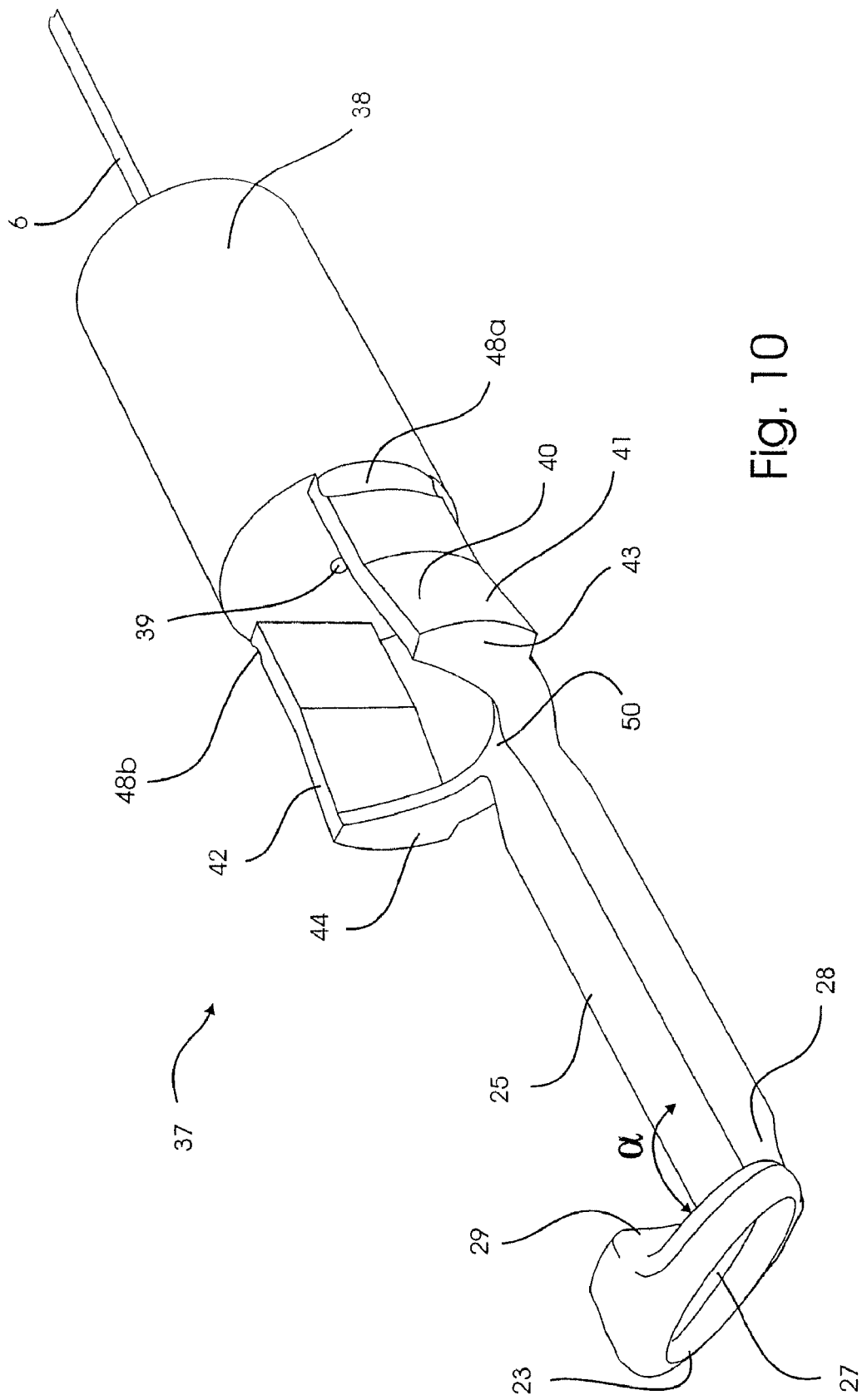
Figure 12:
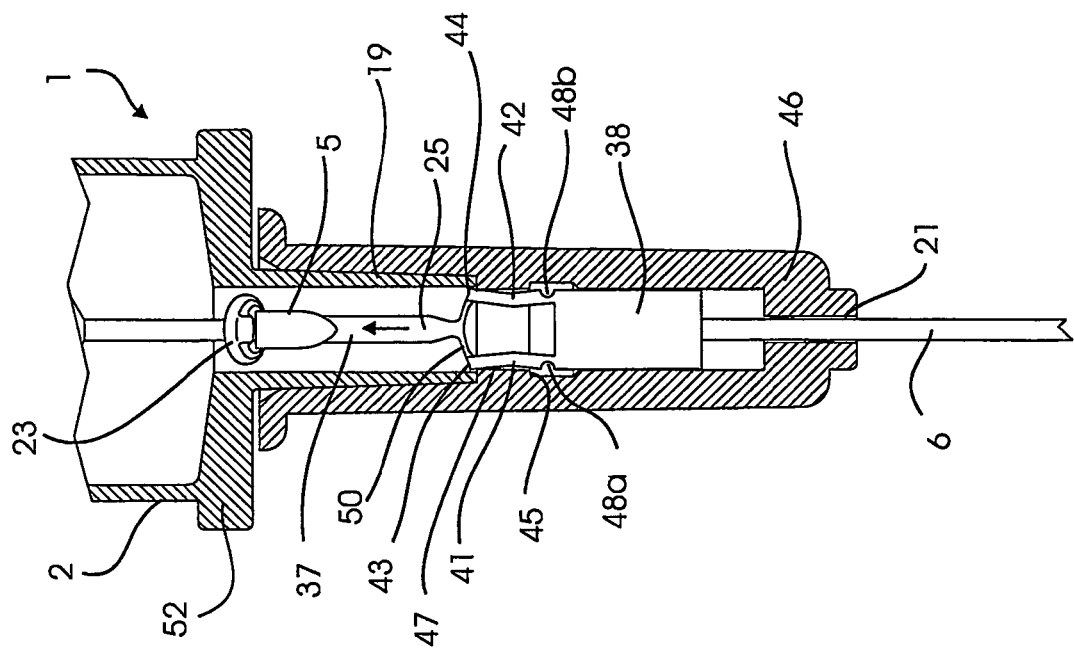
Figure 13:
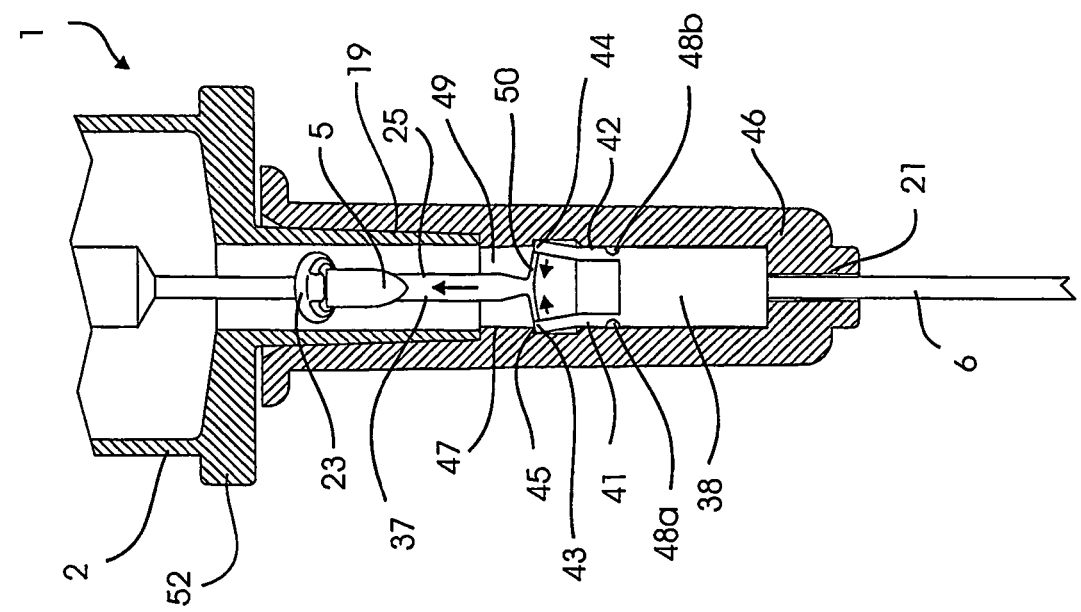

FIG. 10 is a perspective view of a second embodiment of a female coupling part according to the invention, FIG. 11 is partly sectional view of the syringe modified to use the second embodiment of a female coupling part according to the invention shown in FIG. 10 in an assembled condition prepared for injection, FIG. 11a is an enlarged view of the engagement of a modified needle hub and the second embodiment of the female coupling, FIG. 12 is the same at the end of the injection stroke where the syringe is emptied, FIG. 13 is the same at the beginning of the withdrawal of the piston.

DETAILED DESCRIPTION OF THE PREFERRED EMBODIMENTS

The novel and unique features of the invention are achieved by incorporating in the syringe a female coupling part that comprises a coupling ring and a male coupling part that comprises a coupling barb for interlocking with the coupling ring.

As mentioned above the coupling comprises two coupling parts, one part is attached to the piston and the other part is attached to the injection needle. During at least part of the injection stroke the coupling parts are advantageously spaced from each other thereby allowing a smooth injection. The piston will meet no hindrance during the main part of the injection stroke and consequently this part of the injection can be made in a conventional manner. The engagement of the coupling parts will take place especially easily when one of the coupling parts is a male coupling part and the other coupling part is a female coupling part. The male coupling part may preferably be provided on the piston and the female coupling part attached to the injection needle, however the reverse arrangement is also within the scope of the invention. During the injection stroke the coupling parts will approach each other and at the end of this stroke the two couplings parts will engage each other.

The coupling barb of the male coupling part is by means of the compressive force on the piston smoothly forced through the opening of the coupling ring of the female coupling part so that that the remaining part of the injection stroke can take place without discontinuation and without noticeable interruptions. No extra compressive forces need to be applied to the piston in order to enable engagement of the coupling parts. As a result no impact is made on the injection zone upon engagement.

The attachment of the female coupling part, preferably to the injection needle, is advantageously facilitated when said female coupling further comprises an attachment socket. In order to distance the socket from the coupling ring and provide sufficient space for the coupling barb of the male coupling during engagement of the two coupling parts a link may advantageously be provided between the socket and the coupling ring.

In a preferred embodiment for the coupling barb according to the invention the barb may be headed or mushroom shaped. A suitable design for a barb is a coupling pin comprising an outer section facing the coupling ring, said outer section being dimensioned to at least approximately fit into the opening of the coupling ring. The barb may preferably further comprise an inner section facing the piston, said inner section having a smaller diameter than the outer section, and a shoulder defined by the two sections.

The tip of the coupling pin may be more or less pointed or tapered to enable the introduction of the tip through the opening of the female coupling ring. Because the diameter of the inner section of the male coupling barb is selected to be smaller than the diameter of the outer section, no or insignificant frictional forces will arise between male and female coupling during the final stages of the injection stroke.

In a preferred embodiment of the coupling ring according to the invention, the coupling ring may at the side of the ring facing the socket have a projection for engaging with the shoulder in the interlocking position between the coupling ring and the coupling barb.

The projection protrudes from the coupling ring opposite the link and may advantageously serve as a guiding face to allow the smooth passage of the outer section of the male coupling part through the opening of the female coupling ring. It may be preferred that the link and the projection of the female coupling are arranged mainly parallel to each other at a distance which corresponds mainly to the diameter of the outer section of the coupling pin so that sufficient space is provided for the pin and no undue forces, such as e.g. frictional forces, need to be overcome. Upon withdrawal of the piston the two coupling parts are firmly locked together in a hook and eye manner. The projection and shoulder ensure that it is impossible to disengage the interlocking relationship between the coupling parts.

In an embodiment according to the invention, which is especially comfortable for a patient to use, at least one part of the female coupling is made of a polymer and preferably the entire female coupling is produced of a polymer. Such a polymer preferably has a memory and is selected to be sufficiently rigid to maintain the shape of the female coupling during the engagement stage and at the same time tolerate a deformation especially at the suspension point of the coupling ring at the link.

The coupling ring may preferably be arranged protruding from the link at an obtuse angle thereby also forming an obtuse angle with the coupling pin. During the entrance of the outer section of the coupling barb through the opening of the coupling ring the size of the angle between the coupling ring and the coupling pin will be gradually reduced to 90° or less until the outer section of the coupling barb has passed through the opening and the inner section is allow to move freely while finalizing the injection stroke.

When the piston is pushed forward during injection this resilient receipt of the male coupling part into the female coupling part is allowed to take place in an expediently flexible manner which substantially eliminates the uncomfortable and inconvenient feeling at the injection zone of the collision between the coupling parts. This also eliminates the reluctance among syringe users familiar with said feeling when using conventional disposable syringes. Only a minimum of shock load propagates to the injection needle and the injection zone. Consequently, the angularly arranged coupling ring also serves as a moderator or damper during coupling of the coupling parts.

In the most preferred embodiment according to the invention the piston is attached to the male coupling part and the injection needle is attached to the female coupling part. Preferably a needle hub can be provided for mounting on the second end of the cylinder for closing the opening of said second end. The injection needle is, according to the opening paragraph, slidably accommodated in the needle hub so that the needle can be retracted into the syringe cylinder using the piston rod.

The obtuse angle of the coupling ring will force the retracted injection needle into an oblique angle inside the cylinder so that the needle tip is unable to be forced back through the opening of the second end of the cylinder. Preferably the angle is dimensioned so that the needle will touch the sidewall or the internal end of the cylinder when the needle is retracted into the cylinder. The syringe can be completely disabled if the connection between the piston and the piston rod furthermore has a rupture zone so that the piston rod can be broken off and discarded.

In an alternative embodiment of the disposable injection syringe the female coupling part consist of a socket part for the attachment of the injection needle, a link with the coupling ring, and a second part inserted between the link and the socket part. The second part may have at least one flexible leg with a free end face, which via a bridging member merges into the link. The needle hub may advantageously have an internal annular protrusion with a lower protruding edge for defining a seat for abutment and/or engagement of the end faces on the second part, so that the female coupling part is kept situated in the needle up when pressure force are applied to the needle, for example when penetrating the skin. It is preferred that the legs and the bridging member are flexible for in a simple manner to allow for disengagement of the second part from the seat when the needle and the female coupling are retracted into the cylinder of the syringe to preclude reuse.

The retraction is further facilitated when the internal protrusion inside the cavity of the needle hub delimits a hollow section, which tapers slightly in the direction of the male coupling part. The upper edge of the tapering section constitute a stop face which prevent the needle and the female coupling part from being pushed back into the connection piece.

Referring now to the drawings, the disposable syringe 1 for injecting a fluid into e.g. an individual (not shown) is composed of a tubular cylinder 2 (seen in cross-section), a piston 3, a piston rod 4 with a male coupling part 5, an injection needle 6, a needle hub 7 and a female coupling part 8. The piston rod 4 has a finger handle 9 at a free end 10 opposite the end 11, which is provided with the male coupling part 5. The piston rod 4 comprise a total of four legs 12a, 12b, 12c, 12d (only three are seen in the figure) tapering against the end 11. The piston rod 4 extends into the male coupling part 5, said coupling part 5 being a coupling barb 5, via a first flange 13 and a second flange 14, respectively, for mounting the piston 3 at the end 11 of the piston rod 4. The male coupling barb 5 protrudes from the second flange 14. The first flange 13 is connected to the piston rod 4 via a rupture zone 15.

The piston 3 is e.g. a rubber gasket or one or more O-rings having an external diameter corresponding approximately to the diameter of the aperture of the cylinder 2 to provide liquid tight movement of the piston 3 inside the cylinder 2. The piston 3 may be provided with an e.g. silicone coating for promoting the movement of the piston 3 inside the tubular cylinder 2. The piston 3 has in the case shown a through hole 16 and internal grooves (not shown) for receiving the flanges 13 and 14 of the piston rod 4, however other attachment means, such as retainer spikes or a screw thread, for keeping a piston firmly fixed at a piston rod is within the scope of the invention. The male coupling barb 5 protrudes a distance from the piston 3.

The tubular cylinder 2 is a conventional cylinder with a free opening 17 at a first end 18 and an attachment opening 19 at a second opposite end 20, said attachment opening 19 being the connection piece 19 for the injection needle hub 7. The first end 18 furthermore has a retaining flange 18' for supporting the fingers during the injection.

The needle hub 7 has a through hole 21 through which the injection needle is slidably mounted as will be described in further detail later.

As is seen best in FIG. 2, the female coupling part 8 is composed of a socket 22, a coupling ring 23 and a link 25 inserted between the coupling ring 23 and the socket 22 for distancing the coupling ring 23 from the socket 22 so that sufficient space is provided for the male coupling barb 5. The socket 22 has an axial central through hole 26 in which the injection needle 6 is non-releasably secured for allowing the joint removal of the injection needle 6 and the female coupling 8 during disenabling of the syringe 1. In particular, the male coupling barb 5 is configured and dimensioned to pass through the coupling ring 23 without interlocking as the piston is moved through the hole 27 towards the needle, and the coupling barb 5 interlocks with the coupling ring only as the piston is retracted to move away from the needle. The socket 22 furthermore has a groove 22' for temporarily engaging with complementary means inside the needle hub 7, as will be described further in relation to FIG. 7a.

The coupling ring 23 has a central hole 27 and protrudes at an obtuse angle α from a tapered end 28 of the link 25 opposite the socket 22. Opposite to and substantially parallel to or slightly inclined towards the link 25 the female coupling ring 23 has a projection 29. The projection 29 serves partly for guiding an outer section 31 of the male coupling barb 5 through the central hole 27 of the coupling ring 23 during the injection stroke and partly for grasping a shoulder 30 between the outer section 31 and an inner section 32 of the male coupling barb 5 shown in FIG. 3 during disenabling of the syringe 1, as will be described in further details later.

The outer section 31 of the male coupling barb 5 is substantially missile-shaped for further assisting the movement of this barb 5 in the direction of the arrow as shown in FIG. 3 and thereby providing a smooth passage without surface friction drag through the central hole 27 of the coupling ring 23.

The following FIGS. 4 to 9 shows successive stages of the further use and the subsequent disenabling of the syringe 1 according to the invention.

FIG. 4 shows seen partly in section an initial stage of use of the filled syringe 1 according to the invention prepared for injection. Filling takes place in a conventional manner known to the skilled person by using either a conventional injection needle or the specially adapted needle 6 provided with the female coupling part 8 and needle hub 7. Any air bubbles or undesirable content of air is vented by filling and venting in turns in a conventional observant manner, in which engagement of the coupling parts 5,8 are easily avoided if the needle components 6,7,8, according to the invention are used since the coupling parts 5,8 are spaced apart from each other during at least part of the injection stroke. Venting is continued until the syringe 1 is full of e.g. medicament and free of air, i.e. ready for injection.

As seen best in the fragmentary view FIG. 4a of FIG. 4, the socket 22 of the female coupling part 8 is embedded in the substantially V-shaped cavity of the needle hub 7, and the end 33 of the injection needle 6 opposite the injection edge 34 is firmly mounted in the axially central through hole 26 of the socket 22. The female coupling part 8 is dimensioned to be accommodated inside the connection piece 19 of the cylinder 2 when the needle hub 7 holding the needle 6 is mounted at the connection piece 19. As a result of these dimensions the connection piece 19 is able to enclose the entire female coupling part 8, including the link 25 and the coupling ring 23.

A narrow cavity or recess 35 of smaller diameter than the overall internal diameter of the needle hub is defined at the bottom cavity of the needle hub 7. The recess 35 delimit a breast 35'. When mounted at the connection piece 19, the breast 35' of the recess 35 faces and abut the edge 24' of the orifice 24 of the connection piece 19. Thereby the socket 22 is firmly attached inside the orifice of the connection piece 19 during filling and injection. In the preferred embodiment shown in FIG. 4a the socket 22 protrudes a small distance, e.g. between ¼ and ½ of the total axial length of the socket 22, from the recess 35.

By means of a compressive force on the finger handle 9, the piston 3 with the male coupling barb 5 is forced in the direction of the arrow for expelling medicament out of the cylinder 2 as best seen in the midway injection stage of FIG. 5.

FIG. 6 shows the now completely emptied syringe 1 in an end position with engaging but not interlocking male 5 and female 8 coupling parts and the piston 3 resting at the bottom of the cylinder 2. The details of the syringe 1 in this end position are best seen in the enlarged scale of FIG. 6a. The outer section 31 of the male coupling barb 5 has, without any obstructions passed, partly guided by means of the projection 29, through the central opening 27 of the female coupling ring 23 until the front end of the coupling barb 5 contacts the socket 22 and no further forward expelling motion is possible. The sufficient space inside the connection piece 19 and the flexibility of the female coupling 8, especially the flexibility of the coupling ring 23, allow the coupling barb 5 to pass freely through the coupling ring 23 until the piston 3 reaches the end position at the bottom the syringe 1 in which the syringe is empty and the male and the female coupling parts are fully engaged and both located inside the connection piece 19 surrounded by the needle hub 7.

During engagement of the coupling parts 5,8 the projection 29 allows the male coupling barb 5 to pass through the central hole 27 of the coupling ring 23. Thus, the male member is configured and dimensioned to pass completely through the coupling ring. If necessary the outer section 31 of the male coupling barb 5 exerts a slight pressure on the projection 29 so that the projection 30 29 yields thereby allowing the outer section to pass into the opening of the coupling ring in a smooth manner. After passage the projection 29 returns to its starting position in which it may narrow the diameter of the opening of the female coupling ring 23. In the embodiment shown in the figures the projection 29 overhangs the opening of the coupling ring 23 just a little in order to make it impossible for the coupling barb 5 to escape the coupling ring 23 after engagement. The inner section 32 moves freely and unrestricted inside and through the opening of the coupling ring 23. It is preferred that disenabling of the syringe is initiated immediately after the injection is completed.

In FIG. 7 the piston is shown at the beginning of the retraction during the disenabling stage. The piston 3 is retracted a small distance inside the cylinder 2. Withdrawal takes place, e.g. manually, in the direction of the arrow using the finger handle 9 of the piston rod 4 for initially disengaging the coupling of the groove 22' of the socket 22 and the bead 36 inside the recess 35 of the cavity of the needle hub 7. The engagement of the groove 22' and the bead 36 serves for stable and leak-proofed location of the socket 22 in the recess 35 during mounting of the needle 6 on the connection piece 19. This groove and bead arrangement is optional.

As seen best in the enlarged view of FIG. 7a, the shoulder 30 interlock with the coupling ring 23 during further withdrawal and return of the piston 3 to the initial position seen in FIG. 4 and FIG. 9. The projection 29 and/or the shoulder 30 catches the coupling ring 23 and interlock with said coupling ring 23 so that the coupling parts 5,8 are tightened together during the further withdrawal of the piston rod 4 out of the cylinder 2. The injection needle 6, which is stuck in the axially central through hole 26 of the socket 22 of the female coupling 8, is simultaneously pulled backwards inside the cylinder 2 by sliding through the through hole 21 of the needle hub 7. After full withdrawal of the injection needle 6 into the cylinder 2, the injection needle will be positioned as seen in FIG. 8. The needle hub 7 is left for closing the orifice 24 of the connection piece 19, but this stage is optional.

The obtuse angle α of the coupling ring 23 in relation to the link 25, combined with the flexibility and the elastic suspension of the coupling ring 23 on the link 25, forces the injection needle 6 in an oblique position inside the cylinder 2. The angle α prevents the needle from being forced back out of the orifice 24 of the connection piece 19, thereby completely disenabling the syringe 1. Furthermore, no use of the fingers near the needle edge 34 is needed for the disenabling stage thereby eliminating the risk of the person performing the injection getting pricked.

A final further disenabling stage is seen in FIG. 9. After complete withdrawal of the piston rod 4 out of the cylinder 2 the piston rod 4 is disconnected from the piston 3 at the rupture zone 15. The piston rod 4 is discarded and further manipulations of the syringe 1 are made impossible.

For some applications, especially small volume syringes, the projection 29 is dispensable. However, although optional, it is preferred to include the projection 29 in the majority of the syringes according to the invention. The projection serves for optimally securing the interlocking relationship between the coupling parts 5,8 during withdrawal of the injection needle 6 into the cylinder.

In a second embodiment according to the present invention the disposable syringe 1 utilizes a second embodiment 37 of the female coupling part together with a modified needle hub. This second embodiment is a modification of the female coupling and hub shown in FIGS. 1-9 and for like parts same reference numerals are used. As shown in FIG. 10 the second embodiment for a female coupling has a modified socket 38, consisting of a cylindrical socket part 38 with a through bore 39, in which the needle 6 is firmly attached for establishing fluid communication to the syringe cylinder 2, and a second part 40, which extends from the socket part 38 opposite the needle 6. The second part 40 further extends into the elongated link 25 in a similar manner as described under FIGS. 1-9. The second part 40 consists of two opposite facing diverging legs 41,42 with respective merging free end faces 43,44, which via a bridge 50 further merge into the link 25.

In the empty stage of the syringe and during injection the free end faces 43,44 abut against an annular seat 45 inside the modified needle hub 46 as seen best in the partly sectional view of FIG. 11. A pressure force applied to the needle 6 in the direction opposite the injection stroke direction, for example when the needle point penetrates the skin at an injection procedure, will compel the end faces 43,44 of the diverging legs 41,42 to engage the seats 45, so that the female coupling part 8 can not be displaced and is prevented from being pressed inside the syringe cylinder 2.

As seen best in FIG. 11*a* the modified needle hub 46 has an internal annular protrusion 47, which delimit a hollow section 49 inside the cavity of the hub 46, which tapers slightly in the direction of the male coupling part 5. The lower protruding edge of this annular protrusion 47 defines the seat 45.

As illustrated by means of the arrows FIG. 12 the legs 41,42 is forced to converge against each other when the needle is retracted into the syringe cylinder 2. The drawing power allows the end faces 43,44 to disengage the annular seat 45 and the needle 6 and the female coupling to be fully retracted into the syringe cylinder 2 in the same manner as described for the first embodiment and shown in FIG. 13.

The legs 41,42 is provided with respective grooves 48*a*,48*b* adjacent the cylindrical socket part 40, to enhance inclination of the legs 41,42 to converge and inclination to elongate the second part. The grooves allow the legs to easier bend towards each other when forces are applied to the female coupling part 37 in the direction opposite the injection stroke. The upper edge 51 of the tapering section 49 constitute a stop face which prevent the needle 6 and the female coupling part 37 from being able to be pushed back into the connection piece once retracted.

Medical directives and mandatory standards demands that a needle mounted on a syringe must be able to withstand a force of 40 Newton without it being pushed into the cylinder. By suitable dimensioning of the second embodiment it is possible to achieve a disposable syringe fulfilling this requirement. The further advantage of this embodiment is when a user retracts the needle, the male coupling part, and the coupled female coupling part a force of only 5 Newton is necessary for the female coupling part to disengage from the seat and allowing the needle to be retracted into the housing.

In order to provide a firm grip on the syringe an end flange 52 is provided near the second end 20 on the tubular cylinder 2. This allows one hand to operate the finger handle 9 and the second hand to safely maintain control without slipping off the end of the syringe. The extent of the end flange 52 shown in the figures is relatively small, however different sizes for the flange can obviously be chosen to suit different needs.

According to the invention several modifications of the components of the syringe are possible within the scope of the invention. As an example, the female coupling part and the needle hub can be moulded as one single unit. Also different embodiments for the male and female coupling parts are within the scope of the invention, such as for example a hook and eye system. As an example, the outer section can be designed as a V-shaped hook having two flexible legs, which are squeezed against each other during passage of an eye mounted on the female coupling part. After passage the legs are spread for catching the coupling ring during withdrawal of the piston.

The syringe and coupling parts can be manufactured by any suitable polymer such as polyethylene or polypropylene, or mixtures of polymers. The components can be made of the same polymer or of different polymers dependent on the requirements to be satisfied. It goes without saying that all sizes of syringes can be manufactured according to the invention.

What is claimed is:

1. A disposable injection syringe comprising:
    an injection needle,
    a tubular cylinder having first and second ends with a free opening at the first end,
    an end part having a through hole for slidably accommodating the injection needle at the second end of the cylinder,
    a piston reciprocally accommodated in the cylinder for movement toward and away from the needle,
    a piston rod attached to the piston and extending into the cylinder through the free opening at the first end of the cylinder,
    a coupling for interlocking the piston and the injection needle, wherein the coupling further comprises male and female coupling parts, one of which is attached to the piston and the other of which is attached to the injection needle, with the coupling parts being initially spaced from each other, and wherein the female coupling part comprises a coupling ring, and the male coupling part comprises a coupling barb for interlocking with the coupling ring only when the piston moves away from the needle,
    wherein the female coupling part further comprises a socket for attachment of the injection needle, and a link between the socket and the coupling ring, and the female coupling part further comprises a second part inserted between the link and the socket, the second part having at least one flexible leg with a free end face which merge via a bridging member into the link, and a needle hub having an internal annular protrusion with a lower protruding edge defining a seat for abutment or engagement of the end face of the second part.

2. The disposable injection syringe of claim 1, wherein the internal protrusion assists in defining a hollow section inside the cavity of the needle hub which tapers in the direction of the male coupling part.

3. The disposable injection syringe of claim 2, wherein the coupling barb is a coupling pin comprising an outer section facing the coupling ring, wherein the outer section at least approximately fits into the opening of the coupling ring, an inner section facing the piston, said inner section having a smaller diameter than the outer section, and a shoulder defined by the outer and inner sections.

4. The disposable injection syringe of claim 3, wherein the coupling ring includes a projection at a side thereof with the coupling ring facing the socket, and the projection engages the shoulder in interlocking position when the coupling ring and the coupling pin are interlocked.

5. The disposable injection syringe of claim 4, wherein the projection protrudes from the coupling ring opposite the link, and the link and projection are spaced by a distance that corresponds mainly to the diameter of the outer section of the coupling pin.

6. The disposable injection syringe of claim 3, wherein the coupling ring forms an obtuse angle $\alpha$ with the coupling pin.

7. The disposable injection syringe of claim 3, wherein the outer section of the coupling pin is tapering against the tip of the pin.

8. The disposable injection syringe of claim 1, wherein the needle hub is configured for mounting on the second end of the cylinder and for closing an orifice of the second end.

9. The disposable injection syringe of claim 2, wherein the second part includes two opposite facing diverging legs with respective merging free end faces which are connected to the link by a bridge, such that during an injection procedure, the end faces of the diverging legs engage the seat so that the female coupling part cannot be displaced and is prevented from being pressed inside the tubular cylinder.

10. The disposable injection syringe of claim 9, wherein, when the needle is retracted into the tubular cylinder, the end faces disengage the seat so that the needle and the female coupling part can be fully retracted into the tubular cylinder.

11. The disposable injection syringe of claim 10, wherein the coupling ring is positioned at an obtuse angle with respect to the coupling barb such that, upon full retraction of the needle into the tubular cylinder, the needle is moved out of alignment with the end part so that the syringe cannot be re-used.

12. The disposable injection syringe of claim 10, wherein the tapered hollow section includes an upper edge which constitutes a stop face that prevents the needle and female coupling part from returning to the end part so that the syringe cannot be re-used.

* * * * *

UNITED STATES PATENT AND TRADEMARK OFFICE
CERTIFICATE OF CORRECTION

| | |
|---|---|
| PATENT NO. | : 7,544,181 B2 |
| APPLICATION NO. | : 11/293033 |
| DATED | : June 9, 2009 |
| INVENTOR(S) | : Axelsson et al. |

Page 1 of 1

It is certified that error appears in the above-identified patent and that said Letters Patent is hereby corrected as shown below:

<u>Column 8</u>:
Line 9, before "29", delete -- 30 --.
Line 36, delete "projection 29 and/or the" and insert -- coupling barb 5 or its --.
Line 37, delete "interlock" and insert -- interlocks --.

Signed and Sealed this

Twenty-first Day of July, 2009

JOHN DOLL
*Acting Director of the United States Patent and Trademark Office*